United States Patent
Johnston et al.

(10) Patent No.: US 9,675,758 B2
(45) Date of Patent: Jun. 13, 2017

(54) INJECTION DEVICE

(75) Inventors: David Johnston, Melbourn (GB);
Rosemary Habeshaw, Melbourn (GB);
Nigel Harrison, Melbourn (GB)

(73) Assignee: Cilag gmBh International, Landis & Gyrstrasse (CH)

(*) Notice: Subject to any disclaimer, the term of this patent is extended or adjusted under 35 U.S.C. 154(b) by 1522 days.

(21) Appl. No.: 11/579,563

(22) PCT Filed: May 27, 2005

(86) PCT No.: PCT/GB2005/002120
§ 371 (c)(1),
(2), (4) Date: Aug. 27, 2008

(87) PCT Pub. No.: WO2005/115509
PCT Pub. Date: Dec. 8, 2005

(65) Prior Publication Data
US 2011/0178469 A1    Jul. 21, 2011

(30) Foreign Application Priority Data
May 28, 2004 (GB) .................................. 0412054.9

(51) Int. Cl.
*A61M 5/20* (2006.01)
*A61M 5/32* (2006.01)

(52) U.S. Cl.
CPC ......... *A61M 5/2033* (2013.01); *A61M 5/3202* (2013.01); *A61M 5/3204* (2013.01); *A61M 5/326* (2013.01); *A61M 2005/206* (2013.01)

(58) Field of Classification Search
CPC .......... A61M 2005/206; A61M 5/2033; A61M 5/3202; A61M 5/3204; A61M 5/326; A61M 5/3287

(Continued)

(56) References Cited

U.S. PATENT DOCUMENTS 1,845,036 A    2/1932    Busher
2,019,382 A    10/1935    Aronson
(Continued)

FOREIGN PATENT DOCUMENTS

CH    518102 A    1/1972
CN    2059579 U    7/1990
(Continued)

OTHER PUBLICATIONS

EPO Search Report dated Mar. 3, 2009 for corresponding patent application, European Patent Application No. 05746490.1.
(Continued)

*Primary Examiner* — Edelmira Bosques
*Assistant Examiner* — Hamza Darb

(57) ABSTRACT

The present invention concerns an injection device with a housing adapted to receive a syringe having a discharge nozzle, the housing having an indicator opening. There is a trigger and a forward drive arranged to act upon the syringe on actuation of the trigger to advance the syringe from a retracted position to an extended position thereby discharging the contents of the syringe through the discharge nozzle. A support member is in contacting juxtaposition with the housing and a return drive is supported by the support member and arranged to act upon the syringe after the contents of the syringe has been discharged so that the syringe can be withdrawn from the extended position to the retracted position. Advantageously, the support member is arranged in the housing so that the second drive does not obscure an inspection of the contents of the syringe through the indicator opening. Hence, it can be clearly determined whether the contents of the syringe have been expelled from the syringe.

7 Claims, 2 Drawing Sheets

(58) Field of Classification Search
USPC ........ 604/134, 136, 111, 138, 137, 135, 110, 604/192, 187, 156, 157, 194, 197
See application file for complete search history.

(56) References Cited

U.S. PATENT DOCUMENTS

| | | | |
|---|---|---|---|
| 2,147,616 A | 2/1939 | Chaput | |
| 2,295,849 A | 9/1942 | Kayden | |
| 2,531,267 A | 11/1950 | Harisch | |
| 2,764,977 A | 10/1956 | Ferguson | |
| 2,828,742 A | 4/1958 | Ashkenaz | |
| 2,854,975 A | 10/1958 | Cohen | |
| 3,076,455 A | 2/1963 | McConnaughey et al. | |
| 3,131,692 A | 5/1964 | Love | |
| 3,320,955 A | 5/1967 | Sarnoff | |
| 3,329,146 A | 7/1967 | Waldman | |
| 3,543,603 A | 12/1970 | Gley | |
| 3,656,472 A | 4/1972 | Moura | |
| 3,702,608 A | 11/1972 | Tibbs | |
| 3,742,948 A | 7/1973 | Post et al. | |
| 3,797,488 A | 3/1974 | Hurschman et al. | |
| 3,797,489 A | 3/1974 | Sarnoff | |
| 3,880,163 A | 4/1975 | Ritterskamp | |
| 3,976,069 A | 8/1976 | Ong | |
| 4,165,739 A | 8/1979 | Doherty et al. | |
| 4,180,070 A | 12/1979 | Genese | |
| 4,185,628 A | 1/1980 | Kopfer | |
| 4,194,505 A | 3/1980 | Schmitz | |
| 4,222,380 A | 9/1980 | Terayama | |
| 4,231,368 A | 11/1980 | Becker | |
| 4,236,516 A | 12/1980 | Nilson | |
| 4,299,238 A | 11/1981 | Baidwan et al. | |
| 4,333,459 A | 6/1982 | Becker | |
| 4,378,015 A | 3/1983 | Wardlaw | |
| 4,394,863 A | 7/1983 | Bartner | |
| 4,403,989 A | 9/1983 | Christensen et al. | |
| 4,407,283 A | 10/1983 | Reynolds | |
| 4,425,120 A | 1/1984 | Sampson et al. | |
| 4,430,082 A | 2/1984 | Schwabacher | |
| 4,521,237 A | 6/1985 | Logothetis | |
| 4,561,856 A | 12/1985 | Cochran et al. | |
| 4,627,835 A | 12/1986 | Fenton, Jr. | |
| 4,636,201 A | 1/1987 | Ambrose et al. | |
| 4,639,250 A | 1/1987 | Rycroft | |
| 4,642,099 A | 2/1987 | Phillips et al. | |
| 4,676,530 A | 6/1987 | Nordgren et al. | |
| 4,717,383 A | 1/1988 | Phillips et al. | |
| 4,744,786 A | 5/1988 | Hooven et al. | |
| 4,787,891 A | 11/1988 | Levin et al. | |
| 4,874,383 A | 10/1989 | McNaughton | |
| 4,874,384 A | 10/1989 | Nunez | |
| 4,929,232 A | 5/1990 | Sweeney et al. | |
| 4,969,870 A | 11/1990 | Kramer et al. | |
| 4,988,339 A | 1/1991 | Vadher | |
| 5,009,646 A | 4/1991 | Sudo et al. | |
| 5,026,349 A | 6/1991 | Schmitz et al. | |
| 5,057,079 A | 10/1991 | Tiemann et al. | |
| 5,092,842 A * | 3/1992 | Bechtold et al. | 604/135 |
| 5,098,400 A | 3/1992 | Crouse et al. | |
| 5,112,119 A | 5/1992 | Cooke et al. | |
| 5,114,406 A | 5/1992 | Gabriel et al. | |
| 5,122,119 A | 6/1992 | Lucas | |
| 5,137,516 A | 8/1992 | Rand et al. | |
| 5,141,496 A | 8/1992 | Dalto et al. | |
| 5,147,325 A | 9/1992 | Mitchell et al. | |
| 5,156,599 A | 10/1992 | Ranford et al. | |
| 5,176,643 A | 1/1993 | Kramer et al. | |
| 5,190,526 A | 3/1993 | Murray et al. | |
| 5,242,416 A | 9/1993 | Hutson | |
| 5,250,026 A | 10/1993 | Ehrlich et al. | |
| 5,250,037 A | 10/1993 | Bitdinger | |
| 5,263,933 A | 11/1993 | Novacek et al. | |
| 5,267,963 A | 12/1993 | Bachynsky | |
| 5,271,744 A | 12/1993 | Kramer et al. | |
| 5,295,965 A | 3/1994 | Wilmot | |
| 5,300,030 A | 4/1994 | Crossman et al. | |
| 5,312,364 A | 5/1994 | Jacobs | |
| 5,330,081 A | 7/1994 | Davenport | |
| 5,330,430 A | 7/1994 | Sullivan | |
| 5,356,395 A | 10/1994 | Chen | |
| 5,358,489 A | 10/1994 | Wyrick | |
| 5,364,369 A | 11/1994 | Reynolds | |
| 5,368,577 A | 11/1994 | Teoh et al. | |
| 5,372,586 A | 12/1994 | Haber et al. | |
| 5,391,151 A | 2/1995 | Wilmot | |
| 5,405,362 A | 4/1995 | Kramer et al. | |
| 5,411,488 A | 5/1995 | Pagay et al. | |
| 5,425,715 A | 6/1995 | Dalling et al. | |
| 5,451,210 A | 9/1995 | Kramer et al. | |
| 5,478,316 A | 12/1995 | Bitdinger et al. | |
| 5,480,387 A | 1/1996 | Gabriel et al. | |
| 5,487,732 A | 1/1996 | Jeffrey | |
| 5,489,256 A | 2/1996 | Adair | |
| 5,503,627 A | 4/1996 | McKinnon et al. | |
| 5,514,097 A | 5/1996 | Knauer | |
| 5,520,653 A | 5/1996 | Reilly et al. | |
| 5,540,660 A | 7/1996 | Jenson et al. | |
| 5,540,666 A | 7/1996 | Barta et al. | |
| 5,540,709 A | 7/1996 | Ramel et al. | |
| 5,567,160 A | 10/1996 | Massino | |
| 5,569,191 A | 10/1996 | Meyer | |
| 5,569,192 A | 10/1996 | van der Wal | |
| 5,575,777 A | 11/1996 | Cover et al. | |
| 5,599,302 A | 2/1997 | Lilley et al. | |
| 5,599,309 A | 2/1997 | Marshall et al. | |
| 5,607,395 A | 3/1997 | Ragsdale et al. | |
| 5,609,577 A | 3/1997 | Haber et al. | |
| 5,609,584 A | 3/1997 | Gettig et al. | |
| 5,611,785 A | 3/1997 | Mito et al. | |
| 5,637,094 A | 6/1997 | Stewart, Jr. et al. | |
| 5,645,536 A | 7/1997 | Whisson | |
| 5,647,845 A | 7/1997 | Haber et al. | |
| 5,649,912 A | 7/1997 | Peterson | |
| 5,658,259 A | 8/1997 | Pearson et al. | |
| 5,665,071 A | 9/1997 | Wyrick | |
| 5,681,291 A | 10/1997 | Galli | |
| 5,697,908 A | 12/1997 | Imbert et al. | |
| 5,702,367 A | 12/1997 | Cover et al. | |
| 5,704,911 A | 1/1998 | Parsons | |
| 5,709,662 A | 1/1998 | Olive et al. | |
| 5,713,866 A | 2/1998 | Wilmot | |
| 5,748,316 A | 5/1998 | Wakabayashi et al. | |
| 5,779,668 A | 7/1998 | Grabenkort | |
| 5,779,677 A | 7/1998 | Frezza | |
| 5,807,334 A | 9/1998 | Hodosh et al. | |
| 5,817,058 A | 10/1998 | Shaw | |
| 5,827,262 A | 10/1998 | Neftel et al. | |
| 5,843,036 A | 12/1998 | Olive et al. | |
| 5,855,839 A | 1/1999 | Brunel | |
| 5,865,795 A | 2/1999 | Schiff et al. | |
| 5,865,804 A | 2/1999 | Bachynsky | |
| 5,868,711 A | 2/1999 | Kramer et al. | |
| 5,879,327 A | 3/1999 | Moreau DeFarges et al. | |
| 5,913,843 A | 6/1999 | Jentzen | |
| 5,928,205 A | 7/1999 | Marshall | |
| 5,954,738 A | 9/1999 | LeVaughn et al. | |
| 5,957,897 A * | 9/1999 | Jeffrey | 604/223 |
| 5,960,797 A | 10/1999 | Kramer et al. | |
| 5,997,513 A | 12/1999 | Smith et al. | |
| 6,007,515 A | 12/1999 | Epstein et al. | |
| 6,015,438 A | 1/2000 | Shaw | |
| 6,017,330 A | 1/2000 | Hitchins et al. | |
| 6,036,675 A | 3/2000 | Thorne et al. | |
| 6,045,534 A | 4/2000 | Jacobsen et al. | |
| 6,068,614 A | 5/2000 | Kimber et al. | |
| 6,077,247 A | 6/2000 | Marshall et al. | |
| 6,083,197 A | 7/2000 | Umbaugh | |
| 6,086,562 A | 7/2000 | Jacobsen et al. | |
| 6,090,070 A | 7/2000 | Hager et al. | |
| 6,090,078 A | 7/2000 | Erskine | |
| 6,090,897 A | 7/2000 | Akasaki et al. | |
| 6,099,503 A | 8/2000 | Stradella | |
| 6,099,504 A | 8/2000 | Gross et al. | |
| 6,123,684 A | 9/2000 | Deboer et al. | |

(56) References Cited

U.S. PATENT DOCUMENTS

| | | |
|---|---|---|
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,162,199 A | 12/2000 | Geringer |
| 6,171,276 B1 | 1/2001 | Adam et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 * | 3/2001 | Stewart, Sr. ............... 604/207 |
| 6,209,738 B1 | 4/2001 | Jansen et al. |
| 6,221,044 B1 | 4/2001 | Greco |
| 6,228,055 B1 | 5/2001 | Foerster et al. |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 | 9/2001 | Safabash et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Alchas et al. |
| 6,569,124 B1 | 5/2003 | Perouse |
| 6,572,581 B1 | 6/2003 | Landau |
| 6,575,939 B1 * | 6/2003 | Brunel ............... 604/187 |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B1 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landau |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard |
| 6,746,429 B2 | 6/2004 | Sadowski et al. |
| 6,746,438 B1 | 6/2004 | Arnissolle |
| 6,767,336 B1 | 7/2004 | Kaplan |
| 6,770,056 B2 | 8/2004 | Price et al. |
| 6,776,777 B2 | 8/2004 | Barrelle |
| 6,783,509 B1 | 8/2004 | Landau et al. |
| 6,793,161 B1 | 9/2004 | Fujita et al. |
| 6,796,967 B2 | 9/2004 | Jensen |
| 6,811,548 B2 | 11/2004 | Jeffrey |
| 6,817,987 B2 | 11/2004 | Vetter et al. |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,939,330 B1 | 9/2005 | McConnell et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,794,434 B2 | 9/2010 | Mounce et al. |
| 7,799,009 B2 | 9/2010 | Niedospial, Jr. et al. |
| 7,811,262 B2 | 10/2010 | Moberg et al. |
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,409,138 B2 | 4/2013 | James et al. |
| 8,409,141 B2 | 4/2013 | Johansen et al. |
| 8,491,530 B2 | 7/2013 | Maritan |
| 8,696,628 B2 | 4/2014 | Grunhut |
| 8,932,264 B2 | 1/2015 | DeSalvo |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach et al. |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |

(56) References Cited

U.S. PATENT DOCUMENTS

| | | |
|---|---|---|
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0094396 A1 | 5/2004 | Lee et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178630 A1 | 8/2006 | Bostrom et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2010/0063444 A1 | 3/2010 | Wikner |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |
| 2014/0257193 A1 | 9/2014 | Bostrom et al. |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |

(56) References Cited

FOREIGN PATENT DOCUMENTS

| | | |
|---|---|---|
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0515473 A1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1228777 A | 8/2002 |
| EP | 1260241 A1 | 11/2002 |
| EP | 0824923 B1 | 7/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 1932558 B1 | 6/2011 |
| EP | 2468330 A1 | 6/2012 |
| EP | 2340863 B1 | 11/2013 |
| EP | 2620174 B1 | 5/2014 |
| EP | 2675509 B1 | 4/2015 |
| EP | 2705861 B1 | 4/2015 |
| EP | 2414003 B1 | 5/2015 |
| EP | 2464401 B1 | 5/2015 |
| EP | 2493531 B1 | 7/2015 |
| EP | 2705862 B1 | 7/2015 |
| EP | 2588173 B1 | 10/2015 |
| EP | 2470241 B1 | 11/2015 |
| EP | 2768556 B1 | 12/2015 |
| EP | 2355872 B1 | 1/2016 |
| EP | 2720738 B1 | 1/2016 |
| EP | 1412000 B1 | 2/2016 |
| EP | 2671606 B1 | 3/2016 |
| EP | 2760507 B1 | 4/2016 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 A1 | 6/1978 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| GB | 2515041 B | 12/2014 |
| JP | 59-115053 A | 7/1984 |
| JP | 2-185261 A | 7/1990 |
| JP | 2-502971 | 9/1990 |
| JP | 2-502971 T | 9/1990 |
| JP | 02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 T | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2007-207611 A | 8/2007 |
| JP | 2008-284177 A | 11/2008 |
| NZ | 335985 A | 4/2001 |
| NZ | 573171 A | 11/2010 |
| NZ | 573350 A | 12/2010 |
| WO | WO 87/07843 A1 | 12/1987 |
| WO | WO 88/08725 | 11/1988 |
| WO | WO 88/10129 A1 | 12/1988 |
| WO | WO 98/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |

(56) References Cited

FOREIGN PATENT DOCUMENTS

| | | |
|---|---|---|
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | WO 03/013632 A2 | 2/2003 |
| WO | WO 03/015846 A2 | 2/2003 |
| WO | WO 03/015853 A2 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/066152 A2 | 6/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 2010/023303 A1 | 3/2010 |
| WO | WO 2012/000835 A1 | 1/2012 |

OTHER PUBLICATIONS

International Search Report dated Sep. 5,2005; International Application No. PCT/GB2005/002117.
International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5,2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.

(56) References Cited

OTHER PUBLICATIONS

International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11170040.
European Search Report dated Aug. 3, 2011; Application No. 11163779.9.
Singapore Search Report dated Mar. 15, 2012; Application No. SG 201007017-5.
European Search Report dated Jul. 20, 2011; Application No. 11163762.5.
Australian Search Report dated Feb. 26, 2008; Application No. SG 200608071-7.
International Search Report dated Sep. 5, 2005; International Application No. PCT/GB2005/002137.
European Search Report dated Feb. 28, 2011; Application No. 10179733.0.
European Search Report dated Mar. 4, 2011; Application No. 10179736.3.
European Search Report dated Jun. 16, 2011; Application No. 11160134.0.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug., 4, 2011; Application No. 11169691.0.
Great Britain Search Report dated Sep. 29, 2006; Application No. GB0610856.7.
Great Britain Search Report dated Sep. 19, 2006; Application No. GB0610861.7.
European Search Report dated Oct. 15, 2013; Application No. 12182553.3.
Great Britain Search Report dated Dec. 9, 2013; Application No. GB1310394.0.
Great Britain Search Report dated Dec. 8, 2013; Application No. GB1310389.0.
Great Britain Search Report dated Dec. 9, 2013; Application No. GB1310402.1.
Great Britain Search Report dated Dec. 9, 2013; Application No. GB1310392.4.
Great Britain Search Report dated Dec. 10, 2013; Application No. GB1310393.2.
Great Britain Search Report dated Dec. 10, 2013; Application No. GB1310372.6.
International Search Report dated Sep. 8, 2014; International Application No. PCT/EP2014/062163.
International Search Report dated Sep. 8, 2014; International Application No. PCT/EP2014/062166.
International Search Report dated Sep. 17, 2014; International Application No. PCT/EP2014/062167.
International Search Report dated Jan. 29, 2015; International Application No. PCT/EP2014/062167.
International Search Report dated Sep. 9, 2014; International Application No. PCT/EP2014/062168.
International Search Report dated Sep. 8, 2014; International Application No. PCT/EP2014/062162.
International Search Report dated Sep. 16, 2014; International Application No. PCT/EP2014/062160.
European Search Report dated Apr. 28, 2015; Application No. 15153304.9.
International Preliminary Report dated Dec. 15, 2015; International Application No. PCT/EP2014/062163.

(56) References Cited

OTHER PUBLICATIONS

International Preliminary Report dated Dec. 15, 2015; International Application No. PCT/EP2014/062166.

* cited by examiner

INJECTION DEVICE

FIELD OF INVENTION

The present invention relates to an injection device of the type that receives a syringe, extends it, discharges its contents and then retracts it automatically. Devices of this general description are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring. The initial action of the drive spring is typically controlled by means of a trigger. Depression of the trigger causes the drive spring to become operative.

BACKGROUND OF INVENTION

It is not uncommon for an injection device that has been previously used (i.e. a device which has been triggered and therefore has had the contents of its syringe discharged) to be mistaken for a device which has not been used. Although injection devices of this type may include an interlock to prevent further triggering of the device, market research has shown that it is beneficial for an injection device to provide some form of indication that the contents of the syringe has been completely discharged. This way, a user is able to determine immediately by visual inspection whether an injection device has been used. In particular, it has been shown that users of injection devices prefer a visual inspection of the actual syringe to see whether its contents has been discharged. With current injection devices, the return spring often surrounds the syringe thereby obstructing the view of the contents of the syringe. Furthermore, the sight of a return spring surrounding a syringe can be unappealing to a user of an injection device.

It is therefore an aim of the present invention to provide an injection device which gives a clear indication of whether the contents of a syringe has been discharged without the inner mechanical elements of the device being seen by a user. As ever, the simplest and cheapest way of achieving this is sought.

SUMMARY OF THE INVENTION

In view of the foregoing, according to the present invention, there is provided a housing adapted to receive a syringe having a discharge nozzle, the housing having an indicator opening; a forward drive arranged to act upon the syringe on actuation to advance the syringe from a retracted position to an extended position thereby discharging the contents of the syringe through the discharge nozzle; a return drive arranged to act upon the syringe after the contents of the syringe have been discharged to withdraw the syringe from the extended position to the retracted position, characterised in that the return drive is arranged in the housing so that it does not obscure an inspection of the contents of the syringe through the indicator opening. Thus, there is a clear indication through the indicator opening of whether the contents of the syringe has been discharged. In addition, the inner mechanical elements of the device cannot be seen by a user. Furthermore, the indicator opening provides a large window which is not obscured and therefore allows the contents of the syringe to be checked for turbidity and the presence of particles indicating whether the contents of the syringe is safe to be injected.

In one embodiment of the present invention, the injection device comprises a support member which is in contacting juxtaposition with the housing and the return drive is supported by the support member.

Preferably, the support member is transparent and positioned between the indicator opening and syringe. This way, the internal contents of the syringe can be viewed. Before actuation, the liquid contents of the syringe will be viewable through the indicator opening. Transparent material that may be used for the support member is any rigid material which allows light to pass through (e.g. clear or opaque materials).

The support member may comprise a cylindrical insert dimensioned to contain the syringe; and a support surface for the return drive.

In one embodiment of the present invention, a first end of the return drive is in contacting juxtaposition with the support surface and a second end of the return drive is in contacting juxtaposition with the syringe. In a second embodiment of the present invention, the syringe carrier is dimensioned to contain the syringe, the cylindrical insert is dimensioned to contain the syringe carrier and a first end of the return drive is in contacting juxtaposition with the support surface and a second end of the second drive is in contacting juxtaposition with the syringe carrier.

Advantageously, the indicator opening is positioned so that a plunger of the syringe is viewable through the indicator opening when the contents of the syringe has been discharged. After discharge of the contents of the syringe, the plunger, which may be coloured with an easily identifiable colour, will be viewable through the indicator opening to indicate that the injection device has been used.

Preferably, the return drive is a helical spring surrounding at least part of the syringe. By surrounding the syringe with the helical spring, a single spring can be employed which is large enough to have a sufficient spring constant to return the syringe into its retracted position.

Advantageously, the indicator opening comprises a transparent insert which allows inspection of the syringe without the syringe being damaged.

BRIEF DESCRIPTION OF THE DRAWINGS

The invention will now be described by way of example with reference to the accompanying drawings, in which.

DETAILED DESCRIPTION OF THE DRAWINGS

Figure 1:
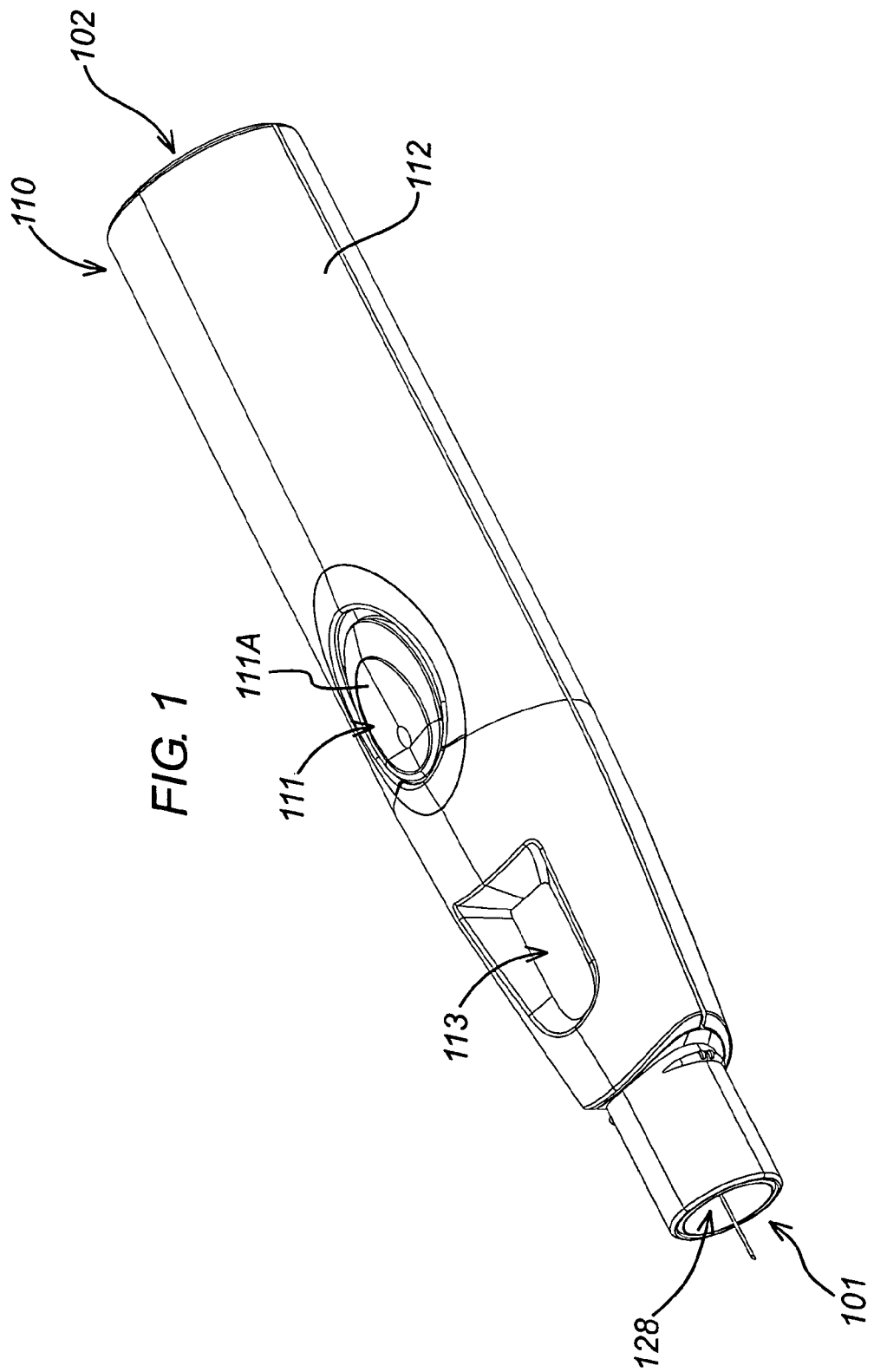
FIG. 1 shows in perspective an injection device of the type to which the present invention is applicable.

FIG. 1 shows an injection device 110 having a housing 112 with a proximal end 101 and a distal end 102. The housing 112 has a trigger 111 which projects through the housing 112 and which can be actuated by pressing down on its upper surface 111a. There is a indicator opening 113 in the housing located adjacent the proximal end 101.

Figure 2:
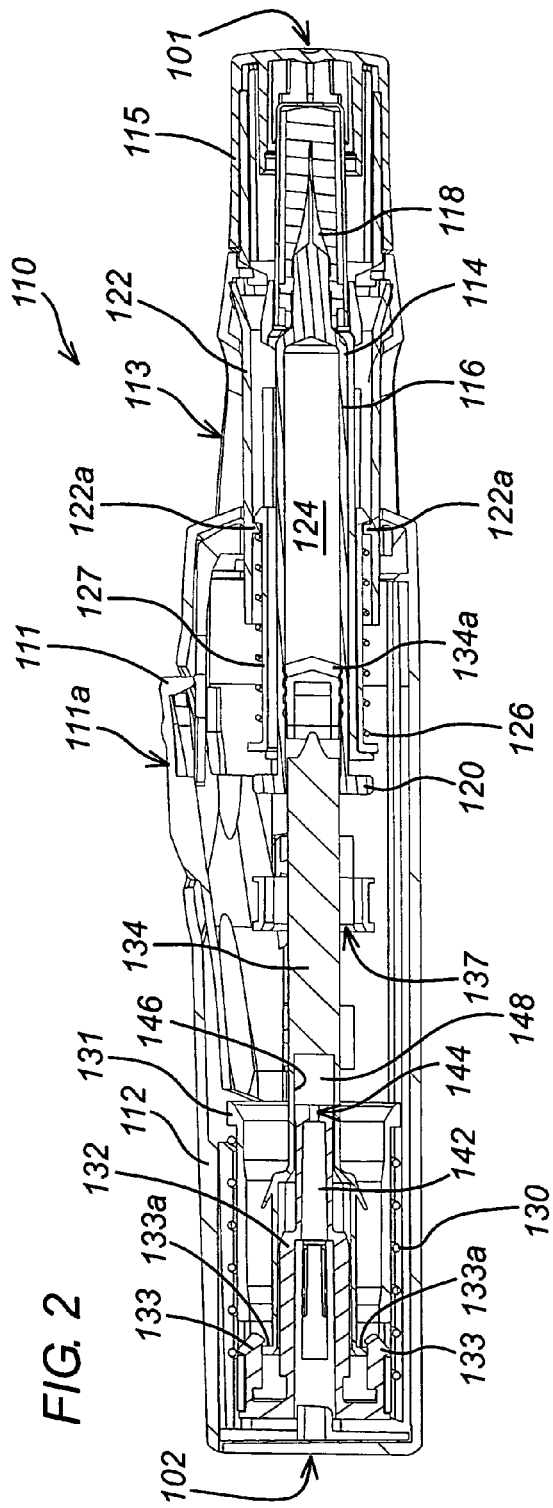
FIG. 2 shows in section the injection device of FIG. 1 before actuation.

FIG. 2 shows the housing 112 containing a hypodermic syringe 114 of conventional type, including a syringe body 116 terminating at one end in a hypodermic needle 118 and at the other in a flange 120. The conventional plunger and bung that would normally be used to discharge the contents of the syringe 114 manually have been removed and replaced with a drive element 134 which includes a bung 134a. This drive element 134 constrains a drug 124 to be administered within the syringe body 116. Whilst the syringe illustrated is of hypodermic type, this need not necessarily be so. Transcutaneous or ballistic dermal and subcutaneous syringes may also be used with the injection device of the present invention. As illustrated, the housing includes a return drive which here takes the form of a compression return spring 126 that biases the syringe 114 from an extended position in which the needle 118 extends from an aperture 128 in the housing 112 to a retracted position in which the discharge nozzle 118 is contained within the housing 112.

The housing 112 includes a support member which, as shown in FIG. 2, takes the form of a cylindrical insert 122. The cylindrical insert 122 has, on its inner surface, a support surface 122a which connects with one end of the return spring 126. The other end of the return spring 126 acts on the syringe 114 via a syringe carrier 127. The support surface 122a is provided, as shown in FIG. 2, by a rim on the inner surface of the cylindrical insert 122. The support surface 122a is positioned beyond the indicator opening 113 away from the proximal end 101 of the housing 112. The return spring 126 connects with the support surface 122a on its end which is located away from the proximal end 101 of the housing 112 and its other end acts on the syringe carrier 127 beyond the support surface 122a from the proximal end 101 of the housing 112. This way, the return spring 126, which surrounds the syringe 114 and syringe carrier 127, cannot be seen through the indicator opening 113 at any time before, during or after triggering of the injection device 110. The cylindrical insert 122 forms a window in the indicator opening 113 formed from transparent material so that the contents of the syringe 114 can be viewed through the indicator opening 113.

At the other end of the housing 112 is a forward drive, which here takes the form of a compression drive spring 130. Drive from the drive spring 130 is transmitted via a multi-component drive to the syringe 114 to advance it from its retracted position to its extended position and discharge its contents through the needle 118. The drive accomplishes this task by acting directly on the drug 124 and the syringe 114. Static friction between the drive element 134 and the syringe body 116 initially ensures that they advance together, until the return spring 126 bottoms out or the syringe body 116 meets some other obstruction (not shown) that retards its motion.

The multi-component drive between the drive spring 130 and the syringe 114 consists of three principal components. A drive sleeve 131 takes drive from the drive spring 130 and transmits it to a first drive element 132. This in turn transmits drive via a damping fluid to a second drive element, the drive element 134 already mentioned.

The first drive element 132 includes a hollow stem 140, the inner cavity of which forms a collection chamber 142 in communication with a vent 144 that extends from the collection chamber through the end of the stem 140. The second drive element 134 includes a blind bore 146 that is open at one end to receive the stem 140 and closed at the other. As can be seen, the bore 146 and the stem 140 defining a fluid reservoir 148, within which the damping fluid is contained.

The trigger 111, when operated, serves to decouple the drive sleeve 131 from the housing 112, allowing it to move relative to the housing 112 under the influence of the drive spring 130. The operation of the device is then as follows.

Initially, the drive spring 130 moves the drive sleeve 131, the drive sleeve 131 moves the first drive element 132 and the first drive element 132 moves the second drive element 134. The second drive element 134 moves and, by virtue of static friction and hydrostatic forces acting through the drug 124 to be administered, moves the syringe body 116 against the action of the return spring 126. The return spring 126 compresses and the hypodermic needle 118 emerges from the exit aperture 128 (shown in FIG. 3) of the housing 112. This continues until the return spring 126 bottoms out or the syringe body 116 meets some other obstruction (not shown) that retards its motion. Because the static friction between the second drive element 134 and the syringe body 116 and the hydrostatic forces acting through the drug 124 to be administered are not sufficient to resist the full drive force developed by the drive spring 130, at this point the second drive element 134 begins to move within the syringe body 116 and the drug 124 begins to be discharged. Dynamic friction between the second drive element 134 and the syringe body 116 and hydrostatic and hydrodynamic forces now acting through the drug 124 to be administered are, however, sufficient to retain the return spring 126 in its compressed state, so the hypodermic needle 118 remains extended.

Before the second drive element 134 reaches the end of its travel within the syringe body 116, so before the contents of the syringe have fully discharged, protrusions (not shown) on the first drive element 132 reach a constriction 137 within the housing 112. The constriction 137 moves the protrusions inwards so that the first drive element 136 is no longer coupled to the second drive element 134. Once this happens, the first drive element 136 no longer acts on the second drive element 134, allowing the first drive element 132 to move relative to the second drive element 134.

Because the damping fluid is contained within a reservoir 148 defined between the end of the first drive element 132 and the blind bore 146 in the second drive element 134, the volume of the reservoir 146 will tend to decrease as the first drive element 132 moves relative to the second drive element 134 when the former is acted upon by the drive spring 130. As the reservoir 148 collapses, damping fluid is forced through the vent 144 into the collection chamber 142. After release of the drive spring 130, some of the force exerted by the drive spring 130 does work on the damping fluid, causing it to flow though the constriction formed by the vent 144; the remainder acts hydrostatically through the fluid and through friction between the first and second drive elements 132, 134, thence via the second drive element 134. Losses associated with the flow of the damping fluid do not attenuate the force acting on the body of the syringe to a great extent. Thus, the return spring 126 remains compressed and the hypodermic needle remains extended.

After a time, the second drive element 134 completes its travel within the syringe body 116 and can go no further. At this point, the contents of the syringe 114 are completely discharged and the force exerted by the drive spring 130 acts to retain the second drive element 134 in its terminal position and to continue to cause the damping fluid to flow though the vent 144, allowing the first drive element 132 to continue its movement.

Before the reservoir 148 of fluid is exhausted, flexible latch arms 133 linking the drive sleeve 131 with the first drive element 132 are no longer forced to engage the drive sleeve 131 by protrusions 133a on the second drive element 134. Once this happens, the drive sleeve 131 acts no longer on the first drive element 132, allowing them to move relative to each other. At this point, of course, the syringe 114 is released, because the forces developed by the drive spring 130 are no longer being transmitted to the syringe 114, and the only force acting on the syringe will be the return force from the return spring 126. Thus, the syringe 114 is now returned to its retracted position and the injection cycle is complete.

All this takes place, of course, only once the cap 115 has been removed from the end of the housing 112. As can be seen from FIG. 2, the end of the syringe 114 is sealed with a boot 123.

Figure 3:
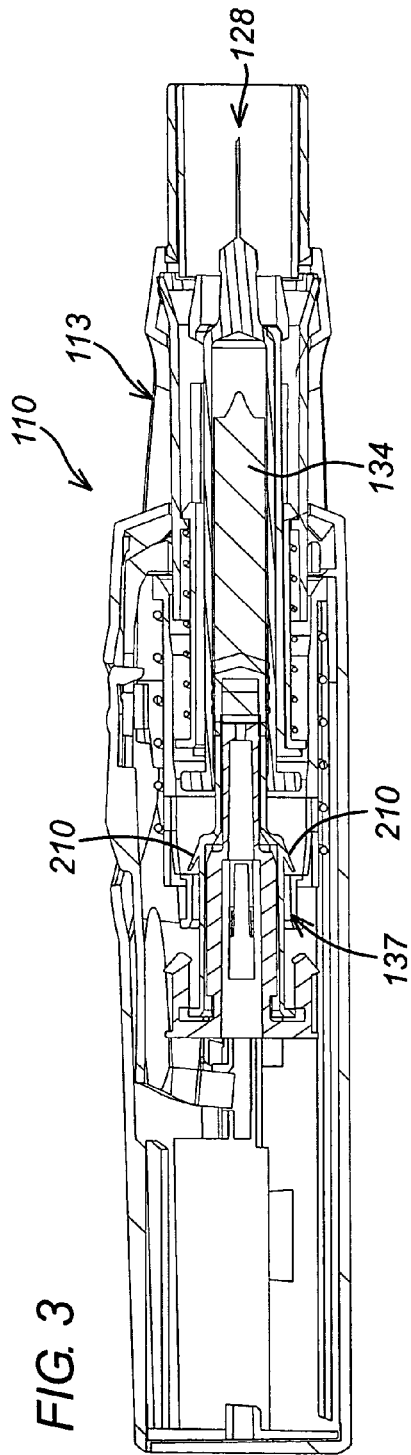
FIG. 3 shows in section the injection device of FIGS. 1 and 2 after actuation.

FIG. 3 shows the injection device 110 after actuation of the injection cycle is complete. The second drive element 134 is located within the syringe body 116 so that it can be viewed through the indicator opening 113. The second drive element 134 is held within the syringe body 116, even though the drive sleeve 131 has been disengaged from the multi-component drive, by forked lugs 210 located on the second drive element 134. The forked lugs 210 have been forced through the constriction 137 so that they prevent rearward movement (i.e. movement in a direction from the proximal end 101 to the distal end 102) of the drive element 134. Thus, the drive element 134 is held in place within the syringe 116 so that it can be viewed through the indicator opening 113. The presence of the second drive element 134 in the syringe body 116 after discharge of the drug 124 acts as an indicator to a user of the device 110 that the device 110 has been operated.

It will of course be understood that the present invention has been described above purely by way of example and that modifications of detail can be made within the scope of the invention.

The invention claimed is:

1. An injection device, comprising:
    a housing that receives a syringe having a discharge nozzle, the housing having an indicator opening;
    a forward drive arranged to act upon the syringe on actuation to advance the syringe from a retracted position to an extended position thereby discharging contents of the syringe through the discharge nozzle;
    a return drive arranged to act upon the syringe after the contents of the syringe have been discharged to withdraw the syringe from the extended position to the retracted position, wherein the return drive is arranged in the housing so that the return drive does not obscure an inspection of the contents of the syringe through the indicator opening; and
    a support member in contacting juxtaposition with the housing, wherein the return drive is supported by the support member and the support member is formed of a transparent material and positioned between the indicator opening and syringe.

2. An injection device according to claim 1 wherein the support member comprises:
    a cylindrical insert dimensioned to contain the syringe; and
    a support surface for the return drive.

3. An injection device according to claim 2, wherein a first end of the return drive is in contacting juxtaposition with the support surface and a second end of the return drive is in contacting juxtaposition with the syringe.

4. An injection device according to claim 2, further comprising a syringe carrier dimensioned to contain the syringe, wherein the cylindrical insert is dimensioned to contain the syringe carrier and wherein a first end of the return drive is in contacting juxtaposition with the support surface and a second end of the return drive is in contacting juxtaposition with the syringe carrier.

5. An injection device according claim 1 wherein the indicator opening is positioned so that a plunger of the syringe is viewable through the indicator opening when the contents of the syringe has been discharged.

6. An injection device according to claim 1 wherein the return drive is a helical spring surrounding at least part of the syringe.

7. An injection device according to claim 1 wherein the indicator opening comprises a transparent window.

\* \* \* \* \*